(12) United States Patent
Gradon et al.

(10) Patent No.: US 8,602,029 B2
(45) Date of Patent: *Dec. 10, 2013

(54) BREATHING ASSISTANCE APPARATUS

(75) Inventors: Lewis George Gradon, Auckland (NZ); Nicholas Charles Alan Smith, Hamilton (NZ); Alastair Edwin McAuley, Auckland (NZ); Mark Joseph Haycock, Basel (CH); Chris Earl Nightingale, London (GB); Daniel Mahon, Christchurch (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1481 days.

This patent is subject to a terminal disclaimer.

(21) Appl. No.: 11/928,779

(22) Filed: Oct. 30, 2007

(65) Prior Publication Data
US 2008/0047557 A1 Feb. 28, 2008

Related U.S. Application Data

(60) Continuation of application No. 10/456,661, filed on Jun. 6, 2003, now abandoned, which is a division of application No. 10/297,951, filed as application No. PCT/NZ01/00110 on Jun. 14, 2001, now abandoned.

(30) Foreign Application Priority Data

| Jun. 14, 2000 | (NZ) | 505154 |
| Jun. 14, 2000 | (NZ) | 505156 |
| Dec. 20, 2000 | (NZ) | 509039 |
| Mar. 12, 2001 | (NZ) | 510520 |

(51) Int. Cl.
*A61M 16/06* (2006.01)

(52) U.S. Cl.
USPC ............ 128/206.24; 128/206.28; 128/206.21; 128/205.25; 128/200.24

(58) Field of Classification Search
USPC .......... 128/857, 863, 200.24, 201.22, 201.23, 128/202.27, 203.29, 205.25, 206.21, 128/206.27, 206.28, 207.11
See application file for complete search history.

(56) References Cited

U.S. PATENT DOCUMENTS

| 2,245,658 | A | | 6/1941 | Erickson |
| 2,931,356 | A | * | 4/1960 | Schwarz ................ 128/206.24 |
| 3,303,845 | A | | 2/1967 | Detmer, III |
| 3,330,273 | A | * | 7/1967 | Bennett ................ 128/206.26 |
| 3,680,555 | A | | 8/1972 | Warncke |
| 3,747,598 | A | | 7/1973 | Cowans |

(Continued)

FOREIGN PATENT DOCUMENTS

| CA | 1039144 | 9/1978 |
| EP | 0 125 210 | 5/1984 |

(Continued)

OTHER PUBLICATIONS

Sep. 21, 2001 International Search Report for Application No. PCT/NZ01/00110 filed on Jun. 14, 2001.

*Primary Examiner* — Annette Dixon
(74) *Attorney, Agent, or Firm* — Knobbe, Martens, Olson & Bear, LLP.

(57) ABSTRACT

A CPAP system for supplying humidified gases to a user is disclosed in which various interfaces are described for gas delivery. A mask cushion including a deformable cushion and thin sheath is described.

14 Claims, 18 Drawing Sheets

(56) References Cited

U.S. PATENT DOCUMENTS

| | | | |
|---|---|---|---|
| 3,815,596 A * | 6/1974 | Keener et al. | 128/205.17 |
| 3,890,966 A | 6/1975 | Aspelin et al. | |
| 3,982,532 A | 9/1976 | Halldin et al. | |
| 4,069,516 A | 1/1978 | Watkins, Jr. | |
| 4,201,206 A | 5/1980 | Kuehn et al. | |
| 4,226,234 A | 10/1980 | Gunderson | |
| 4,665,570 A * | 5/1987 | Davis | 2/428 |
| 4,706,683 A | 11/1987 | Chilton et al. | |
| 4,794,921 A | 1/1989 | Lindkvist | |
| 4,907,584 A | 3/1990 | McGinnis | |
| 4,971,051 A * | 11/1990 | Toffolon | 128/206.26 |
| 5,031,612 A | 7/1991 | Clementi | |
| 5,042,478 A | 8/1991 | Kopala et al. | |
| 5,143,061 A * | 9/1992 | Kaimer | 128/206.24 |
| 5,243,971 A * | 9/1993 | Sullivan et al. | 128/205.25 |
| 5,349,949 A | 9/1994 | Schegerin | |
| 5,438,978 A | 8/1995 | Hardester, III | |
| 5,438,981 A | 8/1995 | Starr et al. | |
| 5,517,986 A | 5/1996 | Starr et al. | |
| 5,570,689 A | 11/1996 | Starr et al. | |
| 5,592,938 A * | 1/1997 | Scarberry et al. | 128/206.24 |
| 5,647,344 A | 7/1997 | Turnbull | |
| 5,647,357 A * | 7/1997 | Barnett et al. | 128/206.24 |
| 5,724,965 A | 3/1998 | Handke et al. | |
| 5,758,642 A | 6/1998 | Choi | |
| 5,884,624 A * | 3/1999 | Barnett et al. | 128/206.24 |
| 6,112,746 A | 9/2000 | Kwok et al. | |
| 6,244,865 B1 | 6/2001 | Nelson et al. | |
| 6,397,847 B1 * | 6/2002 | Scarberry et al. | 128/206.24 |
| 6,412,487 B1 | 7/2002 | Gunaratnam et al. | |
| 6,460,539 B1 | 10/2002 | Japuntich et al. | |
| 6,467,482 B1 * | 10/2002 | Boussignac | 128/206.24 |
| 6,513,526 B2 | 2/2003 | Kwok et al. | |
| 6,532,961 B1 | 3/2003 | Kwok et al. | |
| 6,536,424 B2 | 3/2003 | Fitton | |
| 6,615,834 B2 | 9/2003 | Gradon et al. | |
| 6,634,358 B2 | 10/2003 | Kwok et al. | |
| D483,477 S | 12/2003 | Ankey et al. | |
| 6,679,257 B1 | 1/2004 | Robertson et al. | |
| 6,679,261 B2 | 1/2004 | Lithgow et al. | |
| 6,701,926 B2 | 3/2004 | Olsen et al. | |
| 6,736,139 B1 | 5/2004 | Wix | |
| 6,789,541 B2 | 9/2004 | Olsen et al. | |
| 6,820,617 B2 | 11/2004 | Robertson et al. | |
| 6,951,218 B2 * | 10/2005 | Gradon et al. | 128/205.25 |
| 6,997,186 B2 | 2/2006 | Robertson et al. | |
| 7,017,576 B2 | 3/2006 | Olsen et al. | |
| 7,219,669 B1 | 5/2007 | Lovell et al. | |
| 2003/0154978 A1 | 8/2003 | Gradon et al. | |
| 2003/0196659 A1 | 10/2003 | Gradon et al. | |
| 2006/0237018 A1 * | 10/2006 | McAuley et al. | 128/206.24 |
| 2008/0047557 A1 * | 2/2008 | Gradon et al. | 128/205.25 |
| 2008/0060657 A1 | 3/2008 | McAuley et al. | |
| 2008/0302366 A1 | 12/2008 | McGinnis et al. | |
| 2009/0223520 A1 * | 9/2009 | McAuley et al. | 128/205.25 |

FOREIGN PATENT DOCUMENTS

| | | |
|---|---|---|
| EP | 1 245 250 | 10/2002 |
| GB | 1 395 391 | 5/1975 |
| JP | 11000397 | 1/1999 |
| JP | 2000-325481 | 11/2000 |
| RU | 2 186 597 | 8/2002 |
| SU | 726692 | 9/1981 |
| WO | 85/03880 | 9/1985 |
| WO | 98/04310 | 2/1998 |
| WO | 98/34665 | 8/1998 |
| WO | 00/57942 | 10/2000 |
| WO | 00/74758 | 12/2000 |
| WO | 00/78384 | 12/2000 |
| WO | 01/26722 | 4/2001 |
| WO | WO 01/95965 | 12/2001 |

* cited by examiner

BREATHING ASSISTANCE APPARATUS

CROSS REFERENCE

This application is a Continuation of U.S. patent application Ser. No. 10/456,661 filed on Jun. 6, 2003, now abandoned, which is a divisional of U.S. patent application Ser. No. 10/297,951 which received a 371 filing date of Mar. 25, 2003, now abandoned, which is a 371 filing of PCT/NZ01/00110 filed on Jun. 14, 2001. Each of the aforementioned patents/applications are hereby incorporated by reference.

FIELD OF INVENTION

This invention relates to patient interfaces particularly though not solely for use in delivering CPAP therapy to patients suffering from obstructive sleep apnoea (OSA).

BACKGROUND OF THE INVENTION

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,243,971 and U.S. Pat. No. 6,112,746 are examples of prior art attempts to improve the mask system U.S. Pat. No. 5,570,689 and PCT publication No. WO 00/78384 are examples of attempts to improve the forehead rest.

Where such masks are used in respiratory therapy, in particular treatment of obstructive sleep apnea (OSA) using continuance positive airway pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. A further requisite of such masks is the washout of gas from the mask to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and any bed partners.

Various approaches have been developed in the prior art to attempt to reduce the noise when CPAP therapy is provided. For example, in PCT Patent Application number WO98/34665 it has been proposed that the vent include a resilient plug with rounded edge apertures to reproduce noise. However, this is not entirely effective in eliminating the extra noise created by a vent at the mask.

In common with all attempts to improve the fit, sealing and user comfort is the need to avoid a concentrated flow of air at any portion of the respiratory tracts. In particular with oral masks or mouthpieces it is a disadvantage of prior art devices that the oral cavity may become overly dehydrated by use of the device, causing irritation and possible later complications.

SUMMARY OF THE INVENTION

It is an object of the present invention to attempt to provide a patient interface which goes some way to overcoming the abovementioned disadvantages in the prior art or which will at least provide the industry with a useful choice.

Accordingly in one aspect the invention consists in a device for delivering a supply of gases to a user comprising:

a hollow body including a gases inlet and gases delivery aperture, said gases inlet in use in fluid communication with said supply of gases, a resilient sealing pad adapted to engage around or adjacent to the periphery of said gases delivery aperture, and a flexible sealing lip adapted to engage around or adjacent to the periphery of said gases delivery aperture between said resilient sealing pad and a user, and significantly higher in density than said resilient sealing pad, said resilient sealing pad and said flexible sealing lip each including at least a portion shaped to approximate the facial contour of a user, said resilient sealing pad adapted to deform substantially independently of said flexible sealing lip.

In a second aspect the present invention comprises a device for delivering a supply of gases to a user comprising:

a hollow body including a gases inlet and gases delivery aperture, said gases inlet in use in fluid communication with said supply of gases, a resilient sealing pad adapted to engage around or adjacent to the periphery of said gases delivery aperture, and a flexible sealing lip adapted to engage around or adjacent to the periphery of said gases delivery aperture between said resilient sealing pad and a user, said resilient sealing pad and said flexible sealing lip each including at least a portion shaped to approximate the facial contour of a user, said resilient sealing pad adapted to deform substantially independently of said flexible sealing lip.

In another aspect the present invention consists in a cushion, particularly for use with a patient interface supplying gases to a user, comprising:

a resilient sealing pad, and a flexible sealing lip adapted to engage about said resilient sealing pad, where said resilient sealing pad is adapted to deform substantially independently of said flexible sealing lip.

Preferably said resilient sealing pad is a foam cushion.

Preferably said flexible sealing lip is a sealing membrane substantially covering, and substantially thinner than, said cushion.

Preferably said flexible sealing lip has a periphery that has a bead that connects in use to a substantially similar bead formed in said patient interface, in use said resilient sealing pad being disposed between said flexible sealing lip and said patient interface.

Preferably said flexible sealing lip and said resilient sealing pad each have an inner periphery, the inner periphery of said flexible sealing lip extending in use beyond that of the resilient sealing pad.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION

The present invention provides improvements in the delivery of CPAP therapy. In particular a patient interface is described which is quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
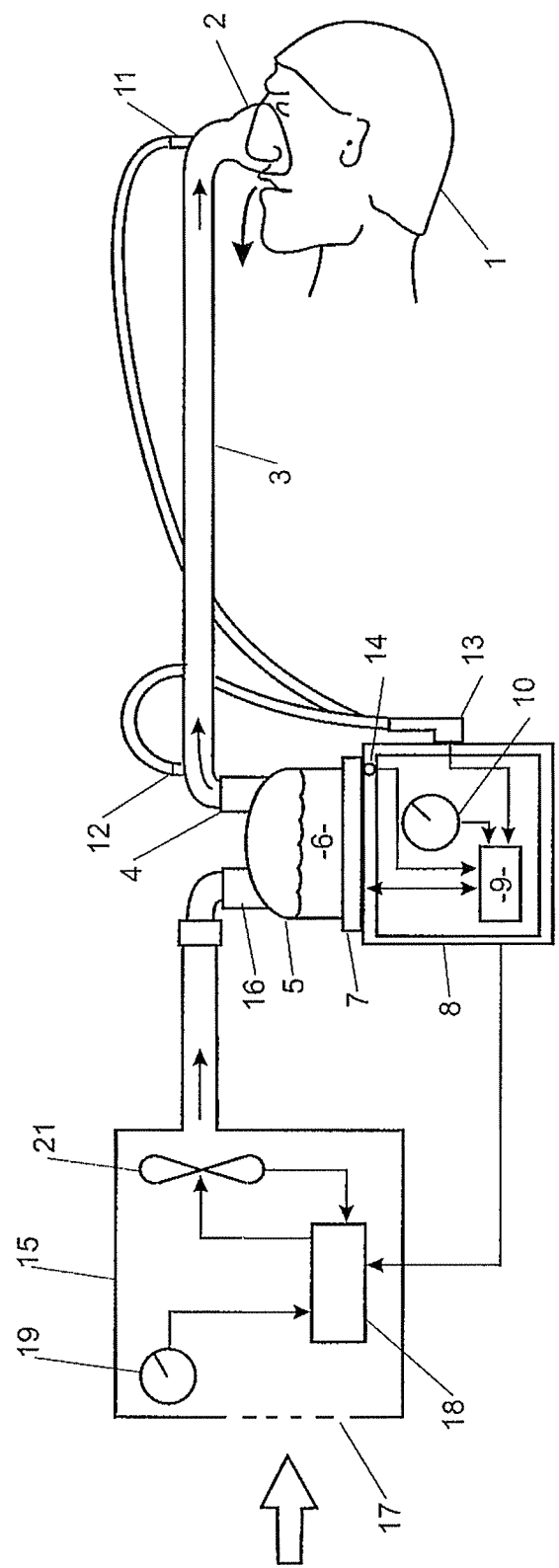
FIG. 1 is a block diagram of a humidified continuous positive airway pressure (system) as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heater wires (not shown) which heat the walls of the conduit to reduce condensation of humidified gases within the conduit. Humidification chamber 5 is preferably formed from a plastics material and may have a highly heat conductive base (for example an aluminium base) which is in direct contact with a heater plate 7 of humidifier 8. Humidifier 8 is provided with an electronic controller 9 which may comprise a microprocessor based controller executing computer software commands stored in associated memory.

Controller 9 receives input from sources such as dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from blower 15 which enters the chamber through inlet 16. Exhaled gases from the patient's mouth are passed directly to ambient surroundings in FIG. 1.

Blower 15 is provided with variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
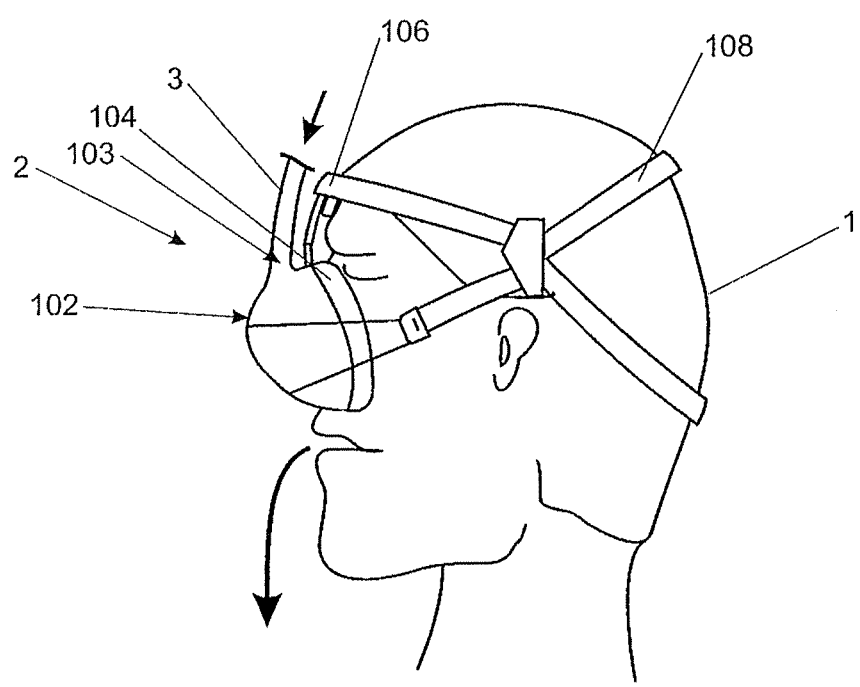
FIG. 2 is an illustration of the nasal mask in use according to the preferred embodiment of the present invention.

According to a first embodiment of the present invention the patient interface is shown in FIG. 2 as a nasal mask. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 18:
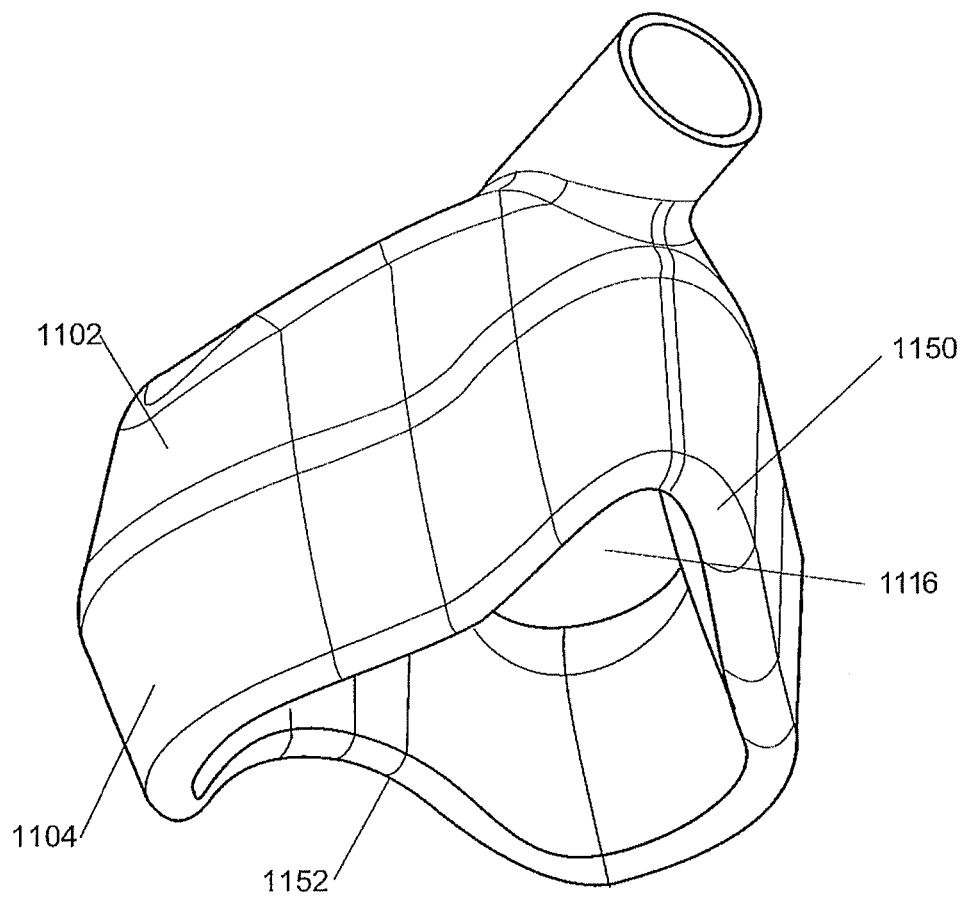
FIG. 18 shows a perspective view of the mask with cushion.
Figure 19:
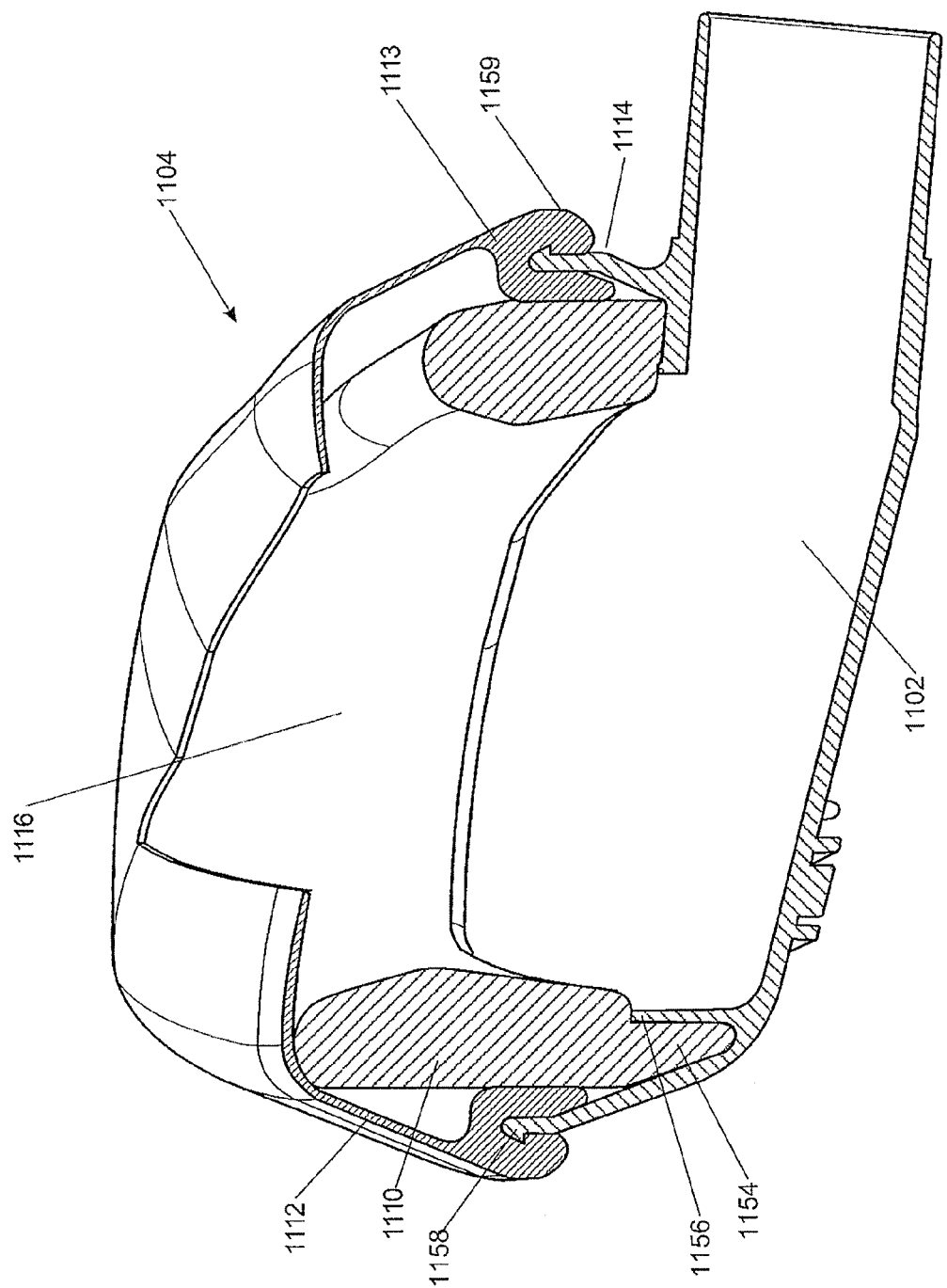
FIG. 19 is a cutaway view of the mask showing the cushion.

Referring now to FIGS. 18 and 19 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 1104 will deform when pressure is applied by the headgear (not shown) to adapt to the individual contours of any particular user. In particular, there is an indented section 1150 intended to fit over the bridge of the user's nose as well as a less indented section 1152 to seal around the section beneath the nose and above the upper lip.

In FIG. 19 we see that the mask cushion 1104 is composed of an inner foam cushion 1110 covered by an outer sealing sheath 1112. The inner cushion 1110 is constructed of a resilient material for example polyurethane foam, and can deform independently of outer sealing sheath 1112 in order to enable it to distribute pressure evenly along the seal around the user's face formed by sealing sheath 1112. Inner cushion 1110 can also act as a secondary seal. The inner cushion 1110 is located around the outer periphery 1114 of the open face 1116 of the hollow body 1102. The open face 1116 acts as a gases delivery aperture to deliver gases to a user. Similarly the outer sheath 1112 may be commonly attached at its base 1113 to the periphery 1114 and loosely covers over the top of the inner cushion 1110.

Figure 20:
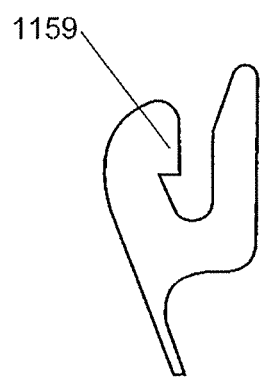
FIG. 20 is a cutaway view of the periphery of the outer membrane.
Figure 21:
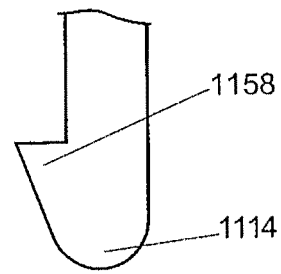
FIG. 21 is a cutaway view of the periphery of the mask body portion.

In the preferred embodiment shown in FIGS. 19-21 the bottom of the inner cushion 1110 fits into a generally triangular cavity 1154 in the hollow body 1102. The cavity 1154 is formed from a flange 1156 running mid-way around the interior of the hollow body.

The outer sheath 1112 fits in place over the cushion 1110, holding it in place. The sheath 1112 is secured by a snap-fit to the periphery 1114 of the hollow body. In FIGS. 20-21 the periphery 1114 is shown including an outer bead 1158. The sheath 1112 includes a matching bead 1159, whereby once stretched around the periphery, the two beads engage to hold the sheath in place.

Forehead Rest

Figure 22:
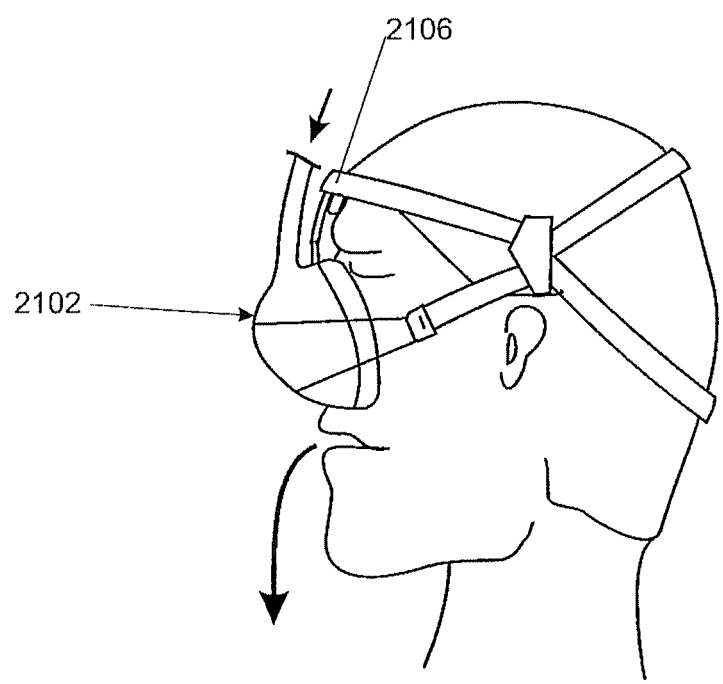
FIG. 22 shows a make with the forehead rest on a user.
Figure 23:
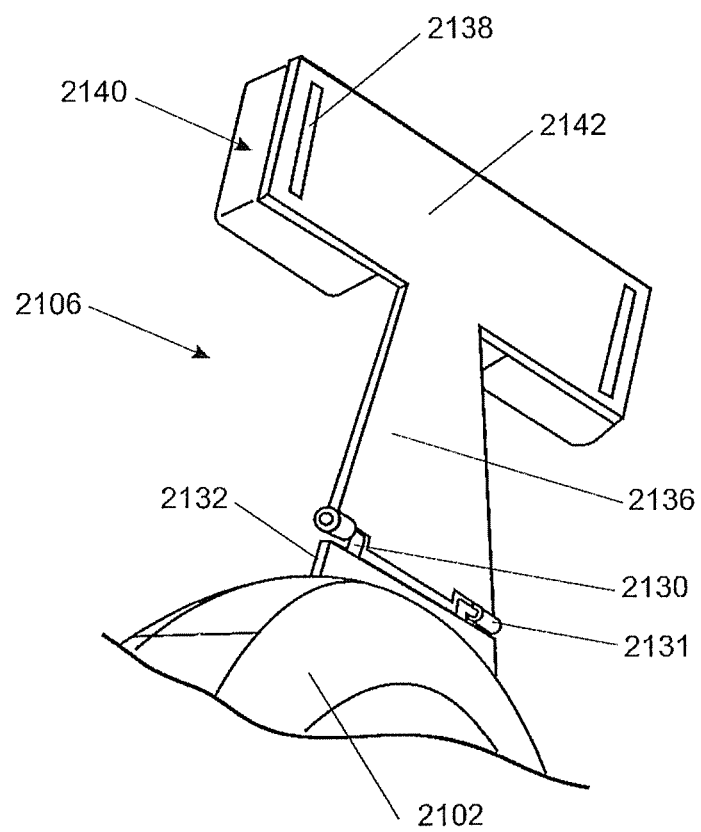
FIG. 23 shows the forehead rest in isolation.

In the preferred embodiment of the present invention the nasal mask 2102 includes a hinged forehead rest 2106 (seen in FIGS. 22 and 23). The attachment of the forehead rest 2106 to the nasal mask 2102 effectively allows the forehead rest 2106 to move freely in proximity to the user but with no lateral movement.

In one form shown in FIG. 23, pins 2130 are provided mounted on a base 2132 attached to the nasal mask 2102. These pins 2130 are co-axial within cylinders 2131 mounted on a bridge member 2136.

At the top end 2142 (around the user's forehead) of the bridge member 2136 harnessing slots 2138 are provided which allow straps from the headgear to be inserted to secure the mask to the headgear. For the users comfort one or more resilient cushions 2140 are provided underneath the top end 2142 of the bridge member 2136, which rest on the forehead of the user. The cushion 2140 might be constructed of silicon or any foam materials as is known in the art for providing cushioning.

For example the forehead rest 2106 described previously may include a weakened section at its base 2132 which allows the joining member 2136 to pivot from the nasal mask 2102. The bridge member extends up to the forehead of the user. In a further alternative the mask may include a vertical upwardly extending inlet. In this case the member 2136 is hinged at its base 2132 to either side of the inlet passage. Again the member would then extend to the forehead.

Alternatively any well-known form of hinge can be used to provide the pivoting action.

Mouthpiece

Now with reference to a further inlet embodiment of the present invention the patient interface 2 is shown in FIGS. 3 to 10 as a mouthpiece. In this embodiment, the mouthpiece 50 includes a vestibular shield 49 being a generally flat and generally rectangularly-shaped member in front elevation having a curved profile that reflects the curvature of a user's jaw and in turn the curvature of the labial vestibule region. A gases passageway extends through the vestibular shield from an inlet 51 to an outlet 52 in much the same way as with the earlier embodiments. In the preferred embodiment the inlet 51 is provided by a flattened oval-shaped connector 53. The outlet 52 has an even more laterally extended flattened oval shape 54. The major differences between the mouthpiece 50 and the embodiments described above are provided on the inner face of the vestibular shield. Most prominently, the mouthpiece 50 includes a tongue depressor 55 extending from the inner face of the vestibular shield 49. The operation of the tongue depressor will be described further on with reference to FIG. 5. The tongue depressor includes a vertical stiffening flange 56 centrally located on its upper surface and extending from the gases outlet 52. In use gases flow easily around the stiffening flange 56 effectively bifurcating the gases outlet 52. The tongue depressor 55 further includes a pair of vertically extending spacers 57 which in use may abut against the roof of the wearer's mouth and ensure that the tongue cannot completely block the air passageway. In the mouthpiece 50 the sealing effect of the vestibular shield 49 against the lips of the user is enhanced by providing teeth abutments of significantly increased thickness than the raised area of the earlier embodiments. In particular, an upper teeth abutment 58 and a lower teeth abutment 59 are provided, with the lower teeth abutment 59 protruding further from the inner face of the vestibular shield 49 than the upper teeth abutment 58. This difference serves to match the typical over-bite of most users. The abutments 58 and 59 are not required to be wider than the gases outlet 52.

A notch 60 is provided centrally in the upper edge of the vestibular shield 49 to accommodate the upper frenal attachment. A slight bead 61 is provided around the edge of the vestibular shield 49 for user comfort, with the vestibular shield 49 otherwise being very thin for additional suppleness.

Figure 6:
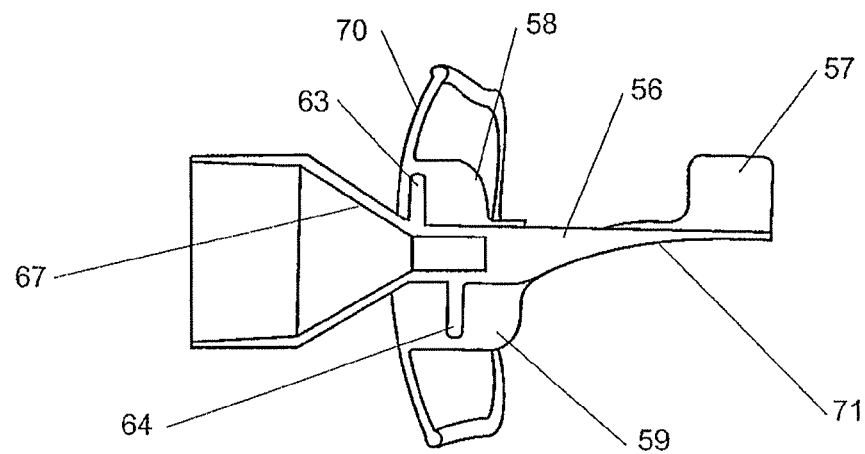
FIG. 6 is a cross-section of the mouthpiece of FIG. 4.

Referring particularly to FIG. 6, in its preferred form the mouthpiece 50 is preferably formed by over-moulding a soft and supple material part 70 over a stiffer material part 67. These can generally be termed the shield part and the passageway-forming insert. The passageway-forming insert preferably includes a pair of upper and lower vertical flanges 63 and 64 to fully engage within the supple material. The passageway-forming insert 67 includes the vertically extending stiffening flange 56 of the tongue depressor 55, together with a curved planar portion 71 forming the backbone of the tongue depressor 55. The vertically extending spacers 57 are of the soft and supple material and are part of the over-moulding 70, as are the upper and lower teeth abutments 58 and 59.

Figure 4:
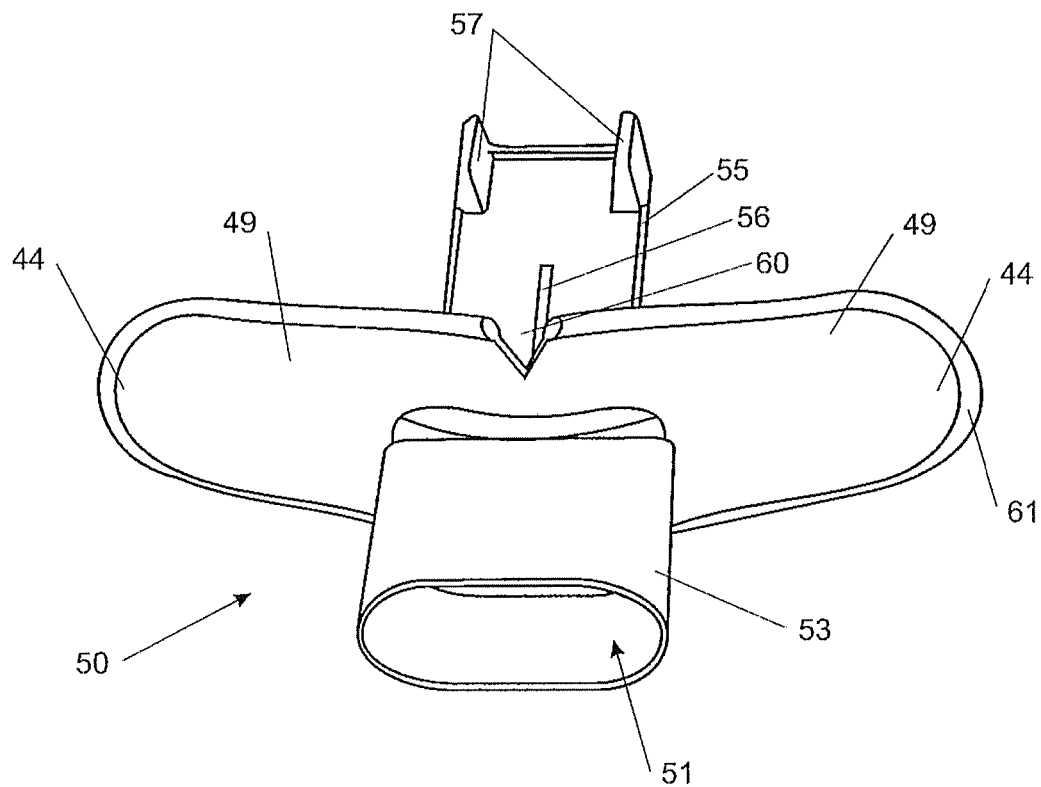
FIG. 4 is a perspective view from above of the mouthpiece.
Figure 5:
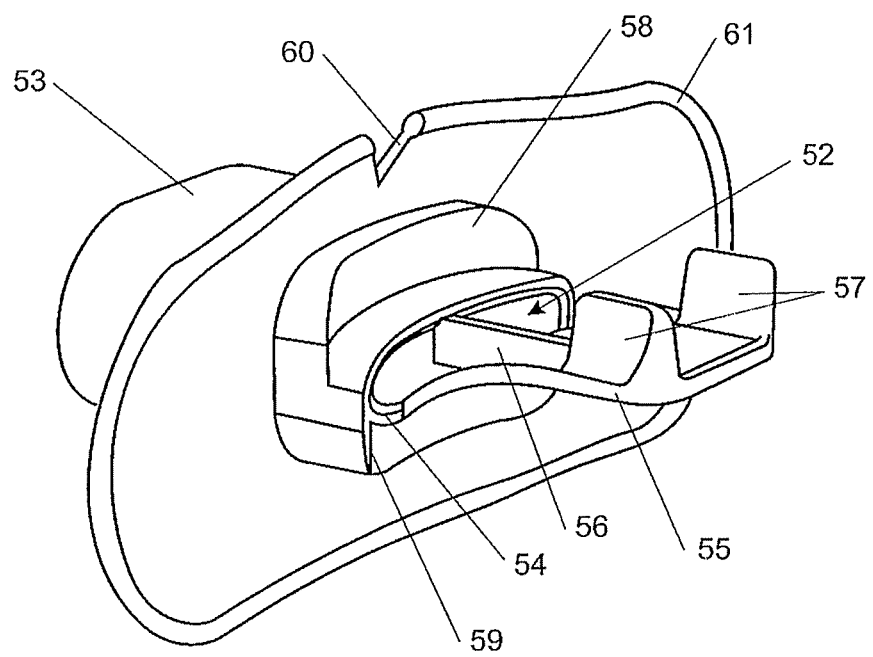
FIG. 5 is a perspective view from one side and from an inward direction of the mouthpiece of FIG. 4.
Figure 7:
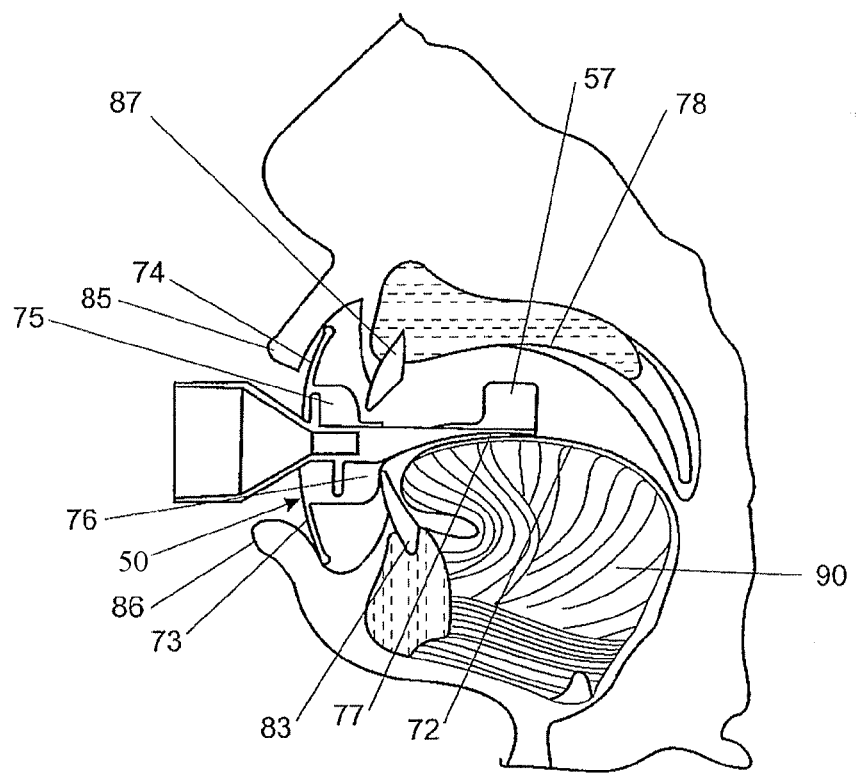
FIG. 7 is a cross-sectional view of the mouthpiece of FIG. 4 and a user with the mouthpiece in place to demonstrate the location and positioning thereof in relation to the main features of the user's anatomy.

Referring now to FIG. 7, use of the mouthpiece according to FIGS. 4 to 6 is depicted. With the present mouthpiece 50, the upper and lower lips 85, 86 are further distended by the abutment action of the abutments 75, 76 against the upper and lower teeth 87, 83 respectively, thus forming a seal of greater pressure between the lips 85, 86 and the upper and lower portions 74, 73, respectively, of the vestibular shield 49. A lower face 77 of the tongue depressor 55 impinges if necessary on the upper surface 72 of the tongue 90 and retains the tongue in the lower portion of the mouth. This ensures a clear gases outlet 52 from the gases passageway through the vestibular shield. The vertically extending spacers 57, if forced by pressure from the tongue, will engage against the roof 78 of the user's mouth and maintain a clear air passageway. This stops the sleeping patient unconsciously blocking the oral passageway and reverting to nasal breathing.

Figure 8:
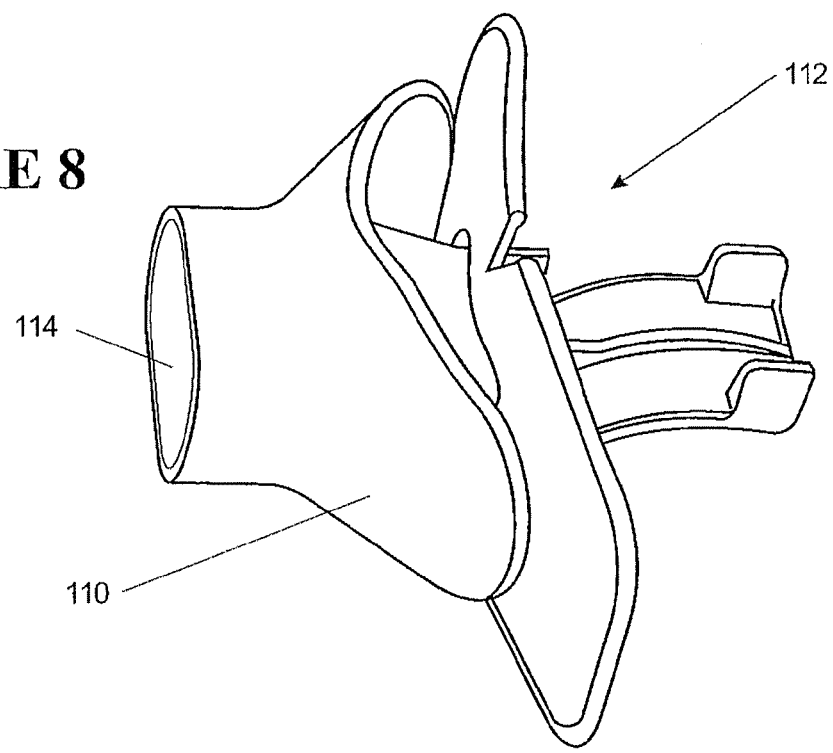
FIG. 8 is a perspective view of the mouthpiece with the outer flap in place.
Figure 9:
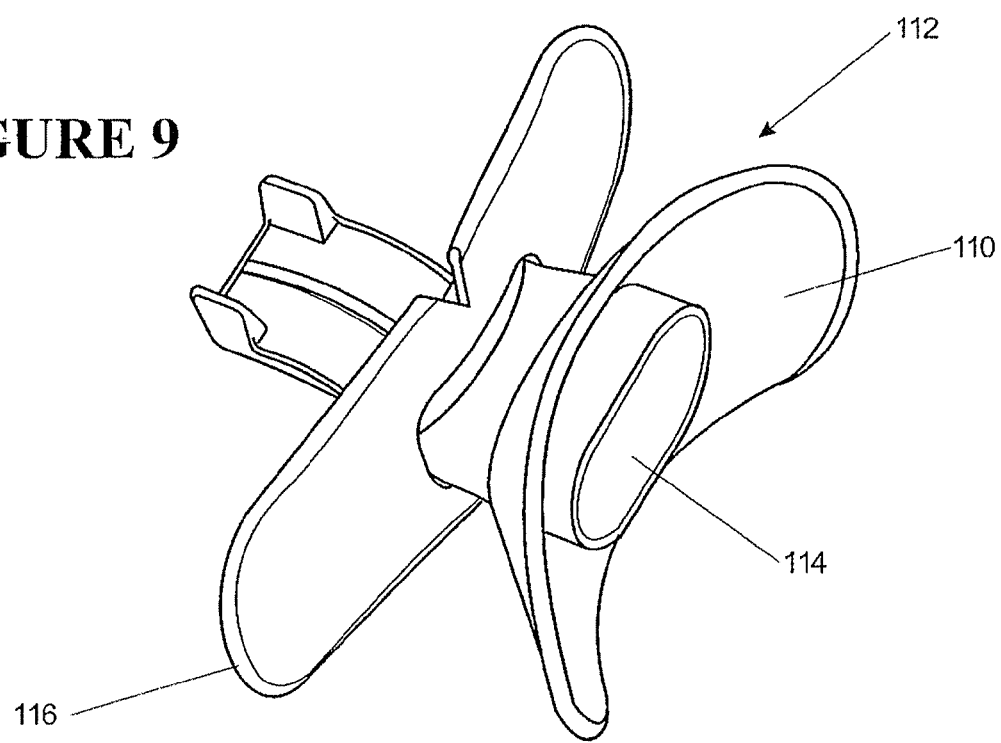
FIG. 9 is a perspective view of the outer flap bent back.

Referring now to FIGS. 8 and 9 of the present invention a mouthpiece is illustrated including an extra-oral sealing flap 110. The flap 110 in its natural bias is tapered, the wide open end of which is shaped to conform to the facial contours around the outside of the mouth of a user. The narrow end joins to a cylindrical section, which is designed to slide over the inlet port 114 of the mouthpiece 112. While this is one method of attachment the flap 100 might also be constructed as an integral part of the mouthpiece 112. The flap 110 needs to be constructed of flexible material, therefore materials such as silicone rubber can be employed to fashion the flap.

The outer flap 110 is seen in FIG. 9, in a bent back position. It will be appreciated that when the mouthpiece 112 is being inserted into the mouth of a user, the outer flap 110 is intended to be in this bent back position to aid insertion. Prior to insertion, the outer flap is bent back by simply pressing on its outer periphery 116, until it snaps into the bent back position, in which it will stay unaided.

Figure 10:
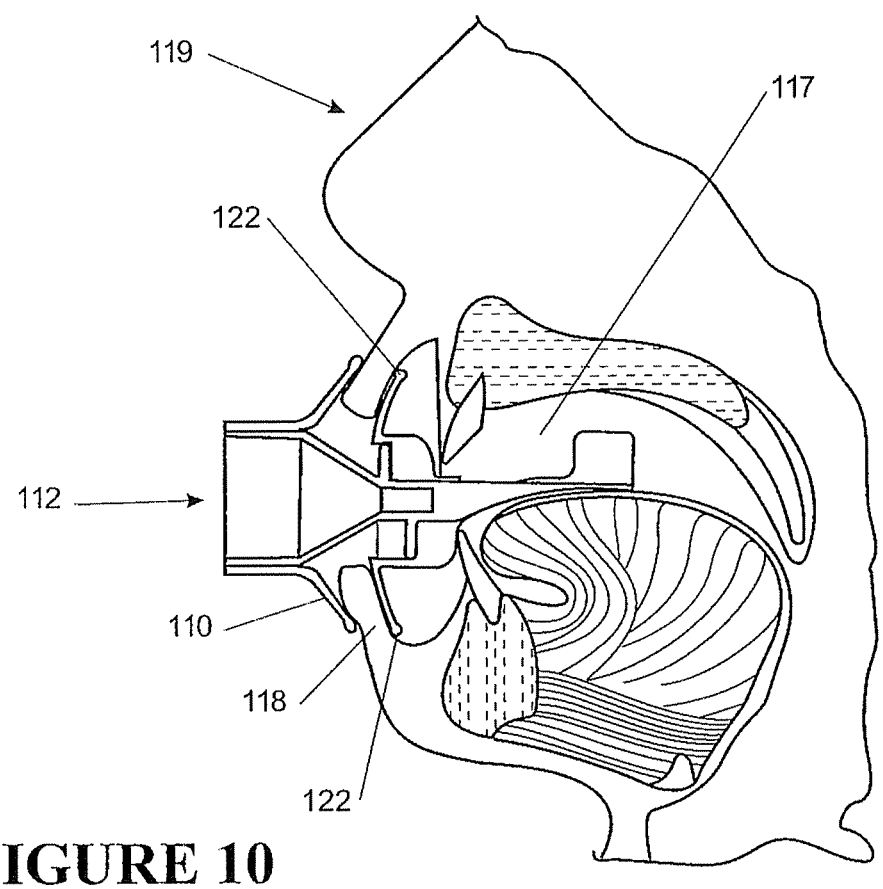
FIG. 10 is a cutaway view of the mouthpiece with the outer flap in use.

In FIG. 10 we see the outer flap 110 in use with the mouthpiece 112 in the mouth 117 of a user 119. Once correctly positioned in the mouth 116, the outer flap 110 may be adjusted into its operational position by pressing on its outer periphery 116 until it snaps back to press against the outside of the mouth 118. Due to the relative position of the vestibular shield 122 and the outer flap 110, the outer flap 110 is unable to fully reach its natural bias and thereby inflicts a compressive force on the outside of the mouth 118.

It will be appreciated that as well as providing a substantially airtight seal the addition of the outer flap provides enough compressive force on the mouth to keep the mouthpiece and conduit in place without the need for straps. This allows the administering of CPAP therapy to be considerably less obtrusive than traditional methods.

Figure 11:
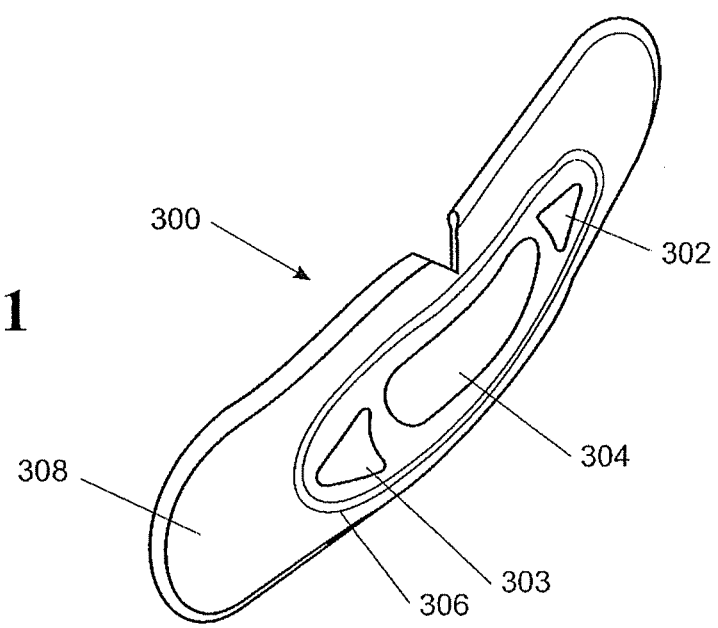
FIG. 11 is a perspective view of the outer flap including the ventilation apertures and moisture barrier.

In a further additional improvement shown in FIG. 11, the outer flap 300 is shown in perspective. Included are ventilation apertures 302, 303 either side of the gases port 304, which are surrounded by a ridge 306 acting as a moisture barrier. The apertures 302, 303 are provided such that any excess moisture leaking from the mouth will migrate to the apertures where they may evaporate. Small vents in the conduit may be used to direct small amounts of pressurised gas at the apertures to aid evaporation. The ridge 306 is included to ensure that no moisture migrates further into the sealing region 308, as this would be detrimental to the sealing properties of the flap.

Interface Connection

Figure 3:
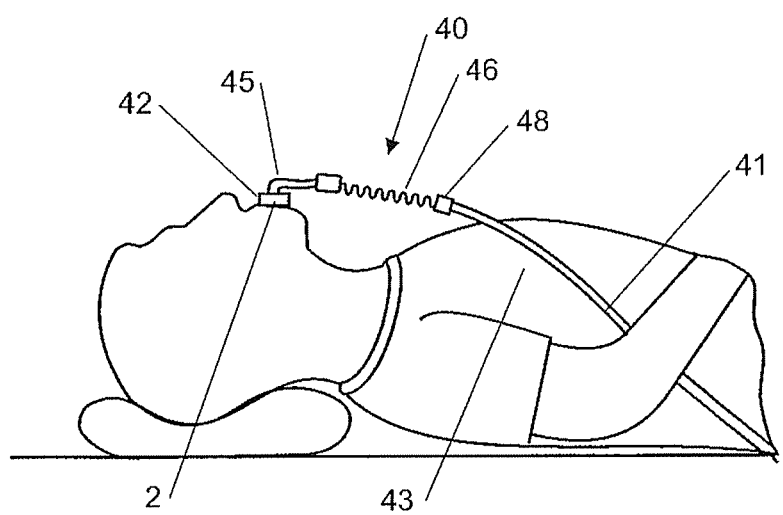
FIG. 3 is a side elevational view of the mouthpiece as being used by a patient.

Attention is now directed to FIG. 3. It has been found that an additional factor in the effectiveness of any patient interface 2 is the manner in which the interface is connected to the breathing circuit 41. The weight of the breathing circuit 41, and any attempted movement of one other of the breathing circuit 41 and the interface 2 relative to the other, is one of the largest influences tending to dislodge the interface 2. It must be noted that the interface 2 must remain in position and maintain a seal during all sleep, when the user has no muscle tone.

The connection 40 as provided in the present invention between the breathing circuit 41 and the interface 2 decouples the interface 2 from the breathing circuit 41. As a result, the connection 40 is effective in reducing the forces placed on the interface 2 by the breathing circuit 41 when the user moves around during sleep. In the preferred sleeping position, the breathing circuit 41 is laid across the chest 43 of the user, and may be secured to the user's bed clothes or sleeping garments. The breathing circuit 41 is preferably laid on the chest of the user to take the weight of the breathing circuit 41 off of the interface 2.

To connect between the gases outlet 42 which is vertical when the user is lying on his or her back and the breathing circuit 41 which is generally horizontal, an L-shaped elbow 45 is incorporated in the connection 40. The elbow 45 may be incorporated in the interface 2. The elbow 45 is formed at a right angle and provides a positive pressure on the interface 2. The elbow 45 may include a swivel joint and may be disconnected from gases outlet 42. The connection 40 further includes an extremely flexible connecting tube 46 provided between the elbow 45 and the breathing circuit 41. The connecting tube 46 is preferably connected to the breathing circuit 41 by a swivel joint 48 for reasons described herein. The breathing circuit 41, while flexible, will necessarily be stiff enough to maintain its integrity over comparatively long lengths, while the connecting tube 46, being only a short length, for example 10 centimeters, merely has to span between the user's mouth and chest, and can thereby be made in a manner that would not be suitable for long lengths. Furthermore, as a result of the short length of the connecting tube 46, the connecting tube 46 does not need to incorporate significant insulation or heating capability. The connecting tube 46 may be formed from a thin plastic membrane supported over a helical or double helical or corrugated supporting ribs. In such a case, the support makes the connection tube 46 laterally flexible and resistant to torsion. The elbow swivel joint 45 allows for movement of the connection tube 46 relative to the interface 2. The swivel joint 48 allows for movement of the connection tube 46 relative to the breathing circuit 41. It is to be understood that one or both of the swivel joints 45, 48 could be eliminated, but the preferred embodiment includes swivel joint 48.

Outlet Vent

The present invention will now be described with reference to the various different embodiments previously described. In order to reduce the noise caused by expiratory gases being expelled from the patient interface 2, the present invention is illustrated in FIGS. 12 to 17 with the elbow connector (previously designated as 45) including an outlet vent. It would be appreciated by one skilled in the art that the elbow connector as described herein will be equally applicable to all proceeding embodiments and all other forms of patient interface for delivering CPAP therapy.

Figure 12:
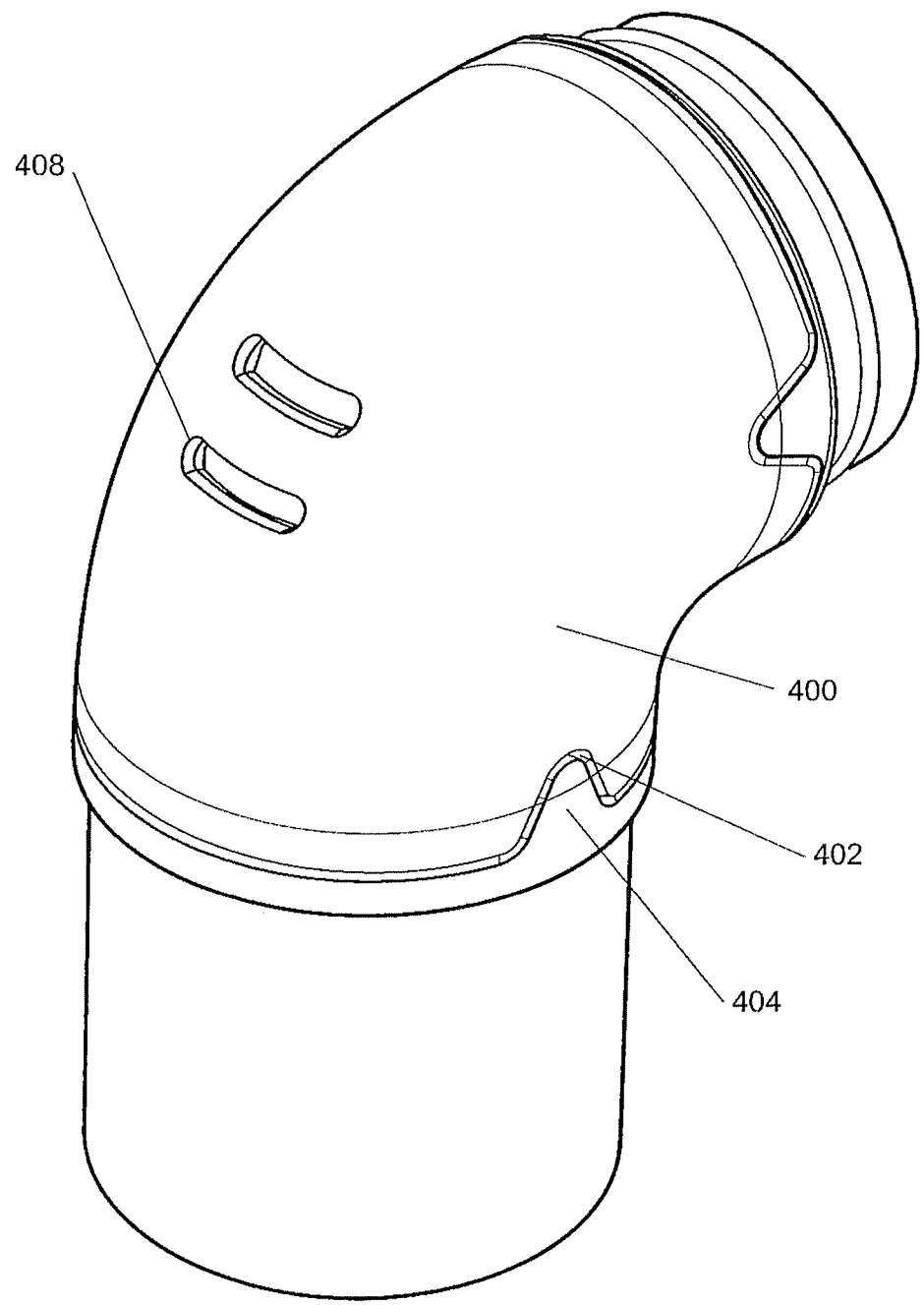
FIG. 12 shows the outlet vent sleeve installed on the elbow.
Figure 13:
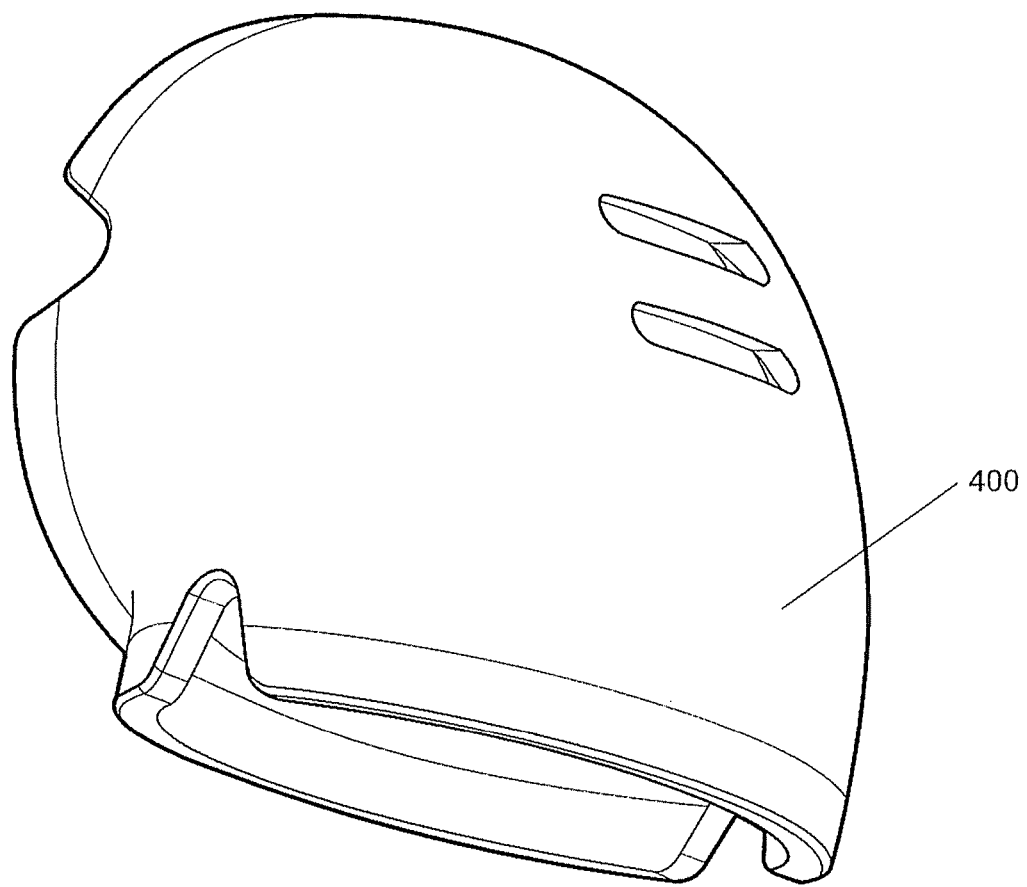
FIG. 13 shows the outlet vent sleeve in isolation.
Figure 14:
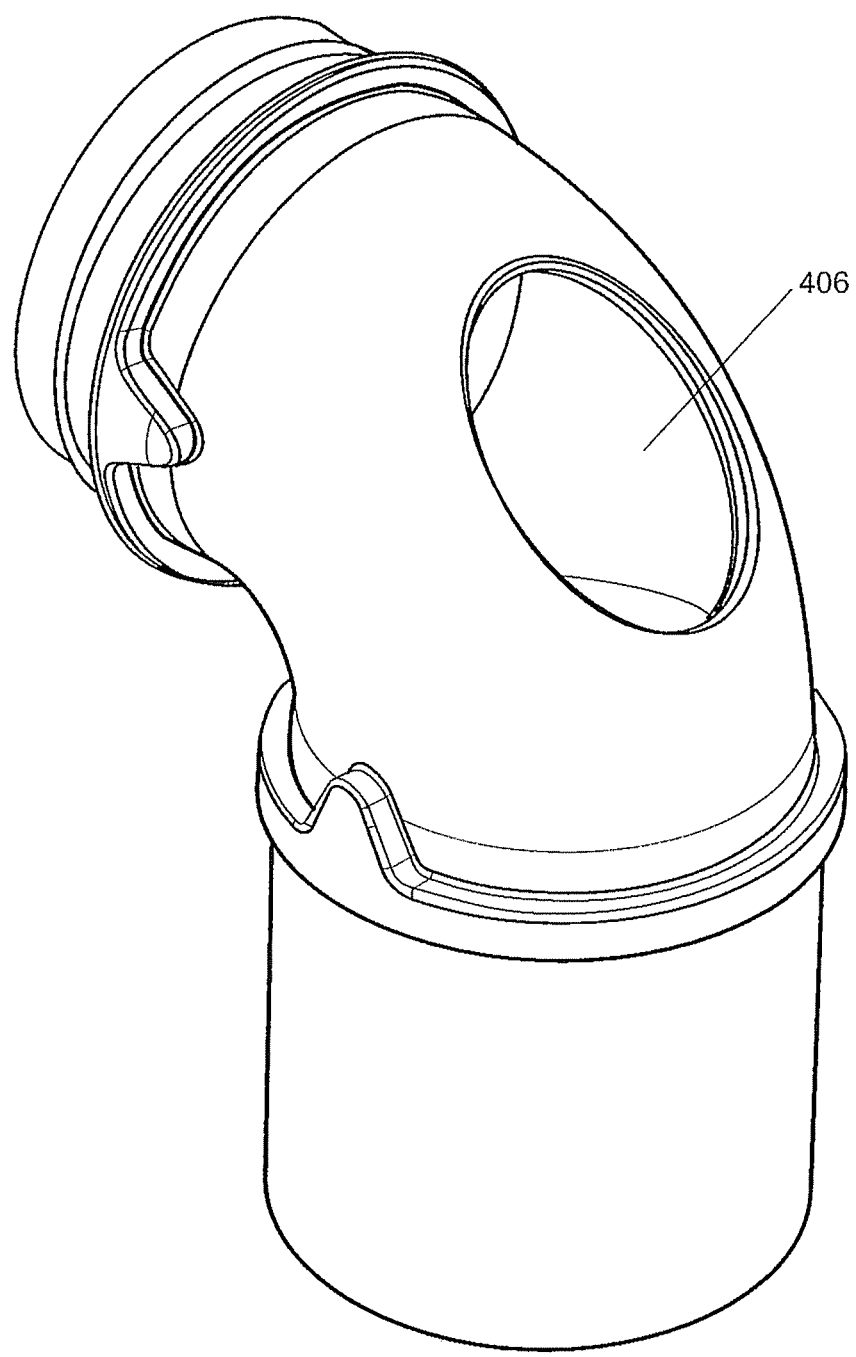
FIG. 14 shows the elbow in isolation.

Referring particularly now to FIGS. 12 to 14, the elbow connector is illustrated including a flexible sleeve 400 which fits overtop of the elbow connector. The sleeve 400 is preferably constructed of silicon, but it will be appreciated by one skilled in the art that a number of other flexible materials will be equally applicable. The sleeve 400 includes locating indents 402 which once installed on the elbow connector match up with and lock into locating notches 404 on the elbow connector. The location is necessary so that the outlet aperture 406 in the elbow connector always matches up with the outlet vents 408 in the outlet sleeve 400. This then prevents the undesirable situation where the sleeve could slip and the outlet vents 408 not match up with the outlet aperture 406 with resulting consequences to the patient.

Figure 15:
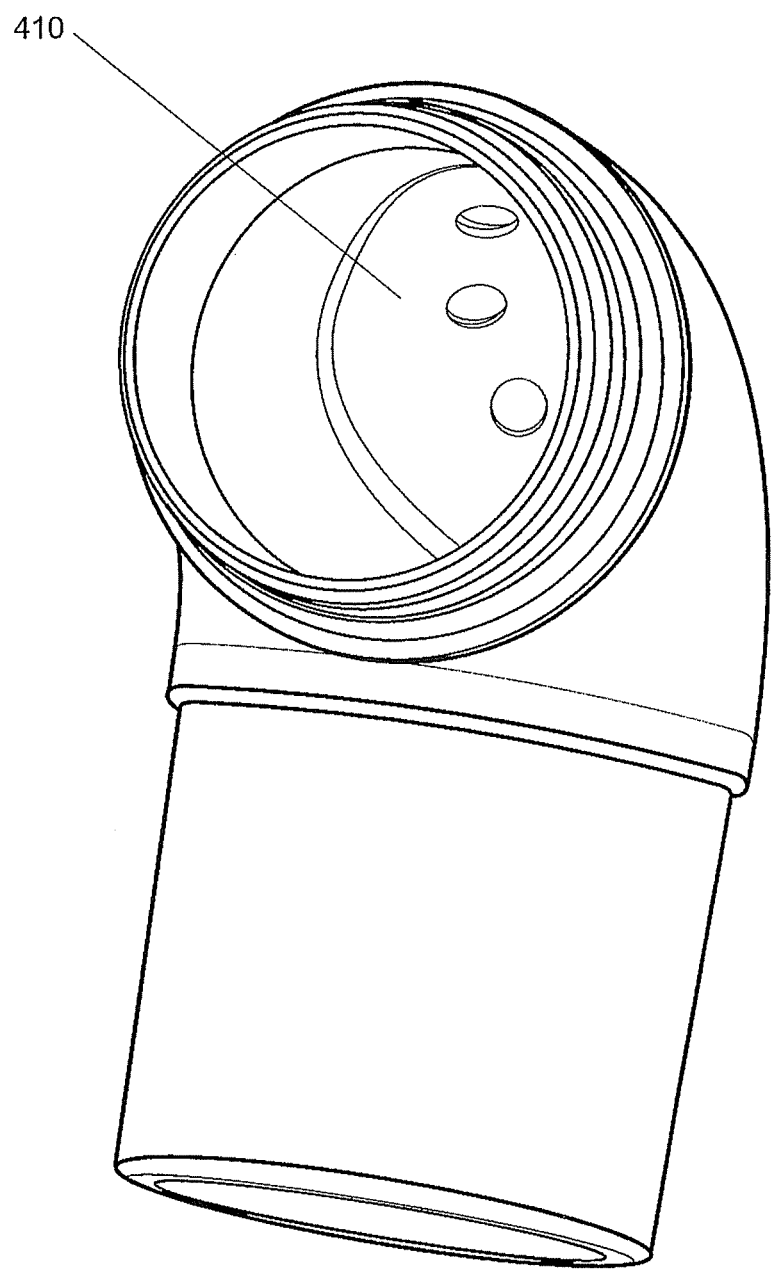
FIG. 15 shows the one piece elbow outlet vent interior.
Figure 16:
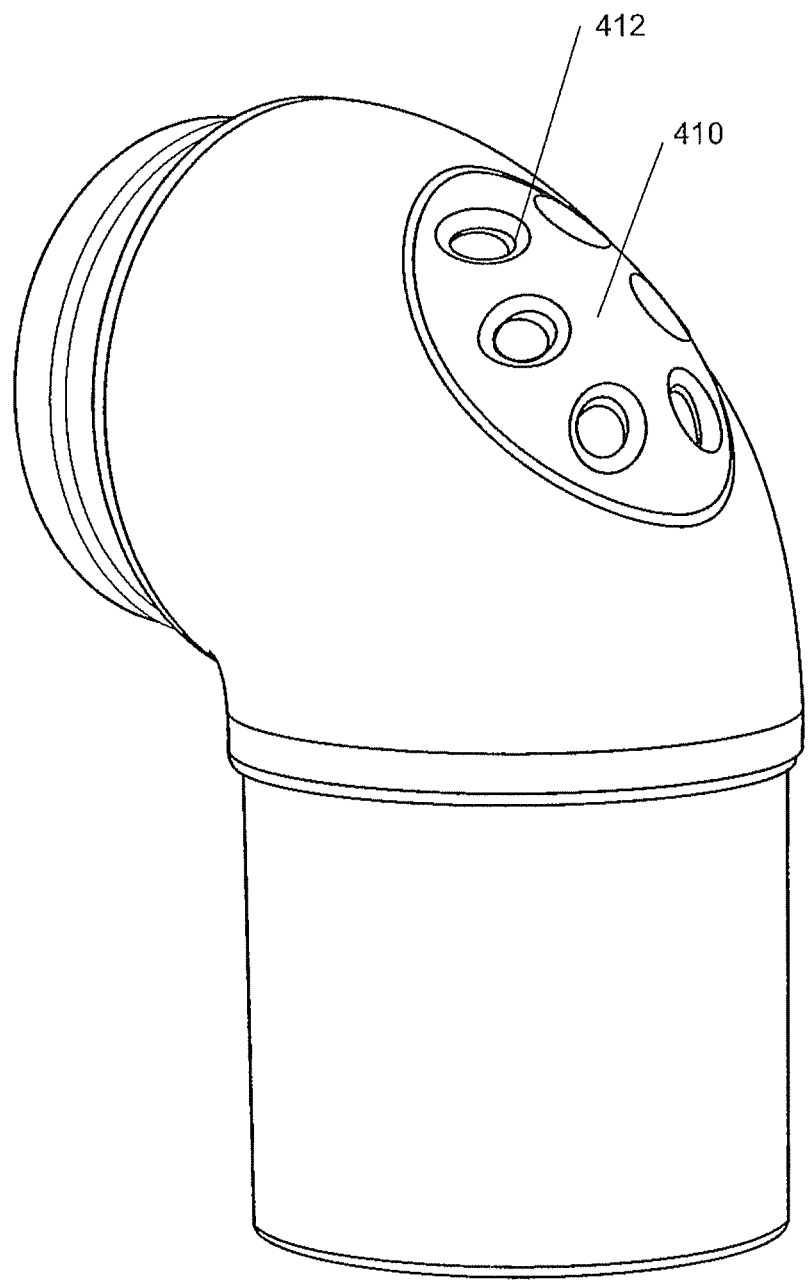
FIG. 16 shows the one piece elbow outlet vent exterior.

Referring now to FIGS. 15 and 16, the present invention is shown with a one-piece elbow. In this case the elbow is preferably constructed of either "Hytrel" plastic or polycarbonate. In this fashion the elbow connector is manufactured to have a thin portion 410 surrounding the outlet vents 412 in comparison to the remainder of the elbow connector which is considerably thicker. The properties of the material chosen for the elbow connector are such that its flexibility is dependent on its thickness. Therefore in the thin portion 410 the elbow connector is relatively flexible and in the remainder is relatively rigid. Accordingly the outlet vents 412, which are also rounded on their periphery are formed in a flexible portion, and therefore achieve the desirable low noise properties when expiratory gases are vented there through.

Flow Diffuser

Figure 17:
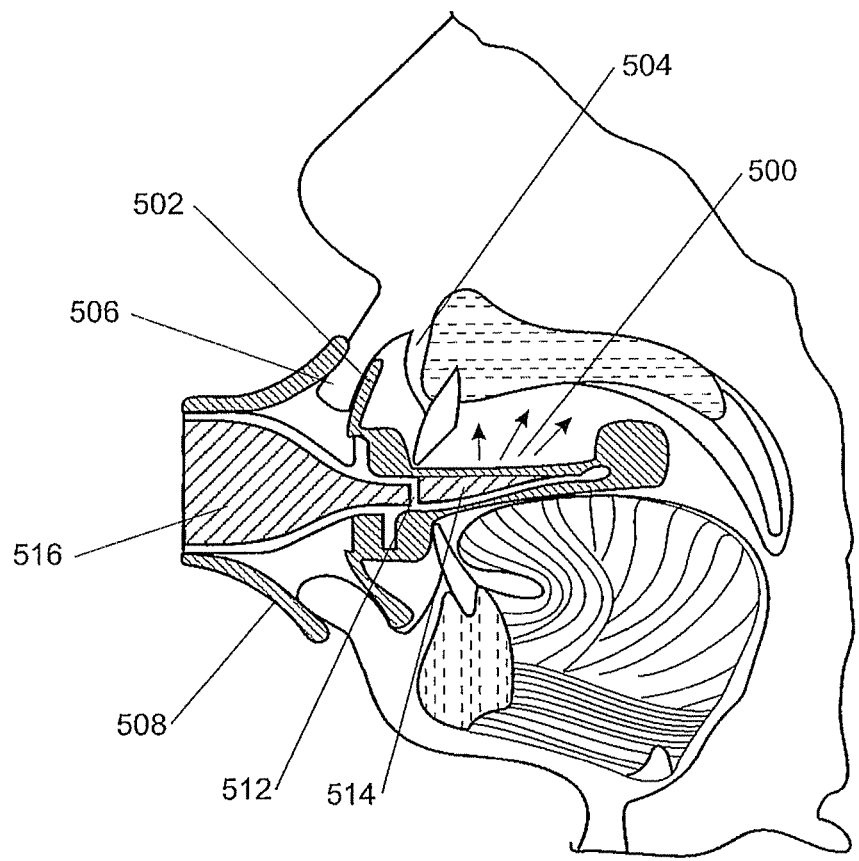
FIG. 17 shows a cross section of the mouthpiece with a dispersing filter.

Referring now particularly to the use of mouthpieces, a further improvement is shown in FIG. 17. It is documented that when CPAP therapy is delivered to patients they often complain of drying of the airways and resulting irritation and discomfort. In particular when a concentrated airflow of under humidified gases flows past the oral or nasal cavities, or the airway of the user then drying and irritation may occur. Accordingly the present invention as illustrated in FIG. 17 includes a mouthpiece with a flow diffuser 500.

As described in the preceding embodiments, the mouthpiece sits with a vestibular shield 502 between the gums 504 and the lips 506 of a user. An outer flap 508 provides compressor force on the lips 506 to keep the mouthpiece in place in the user's mouth. Again the mouthpiece includes a tongue depressor 514 extending into the user's oral cavity.

In the preceding embodiments the delivered gases would flow through passageway 512 in the mouthpiece, causing a relatively concentrated flow of gases to flow through the oral cavity and down the airway. With the flow diffuser 500 fitted overtop of the passageway 512 the flow is defused over the much larger area of the diffuser 500, and therefore both the speed and side effects are reduced.

Alternatively the space between the passageway 512 and the diffuser 500 could be filled with a Humidity Moisture Exchange (HME) material. This would allow moisture through on the inspiratory flow put prevent it passing out an expiration. This would further prevent against the patient's passageways drying out. Further, if the HME material was in the form of foam, then it might also act as the diffuser 500. It will also be appreciated that the HME material could be used in the space 516 all the way out to the elbow connector (not shown) to maximise its effect.

It will be appreciated that by providing such a system the present invention effectively minimises the noise generated by the outward flow of expiratory gases from the mask. The present invention requires little or no maintenance. The present invention also provides a flow diffuser for use with the mouthpiece, which reduces any side effects of orally delivered CPAP therapy and improves user comfort.

The invention claimed is:

1. A cushion, configured for use with a patient interface that is configured to supply gases to a user, comprising:
    a resilient sealing pad comprising a foam cushion; and
    a flexible sealing lip, adapted to engage about said resilient sealing pad,
    wherein said resilient sealing pad is adapted to deform substantially independently of said flexible sealing lip such that said flexible sealing lip may be deformed without deforming the resilient sealing pad; and
    wherein the resilient sealing pad and flexible sealing lip are configured to be independently received within a channel extending at least partially around an opening edge of a patient interface.

2. A cushion according to claim 1 wherein said flexible sealing lip is a sealing membrane substantially covering, and substantially thinner than, said resilient sealing pad.

3. A cushion according to claim 1 wherein said flexible sealing lip has a periphery that has a bead that connects in use to a substantially similar bead formed in said patient interface, in use said resilient sealing pad being disposed between said flexible sealing lip and said patient interface.

4. A cushion according to claim 1 wherein said flexible sealing lip and said resilient sealing pad each have an inner periphery, the inner periphery of said flexible sealing lip extending in use beyond that of the resilient sealing pad.

5. A cushion, configured for use with a patient interface that is configured to supply gases to a user, comprising:
    a resilient sealing pad comprising a compressible material; and
    a flexible sealing lip, adapted to engage about said resilient sealing pad,
    wherein said resilient sealing pad is adapted to deform substantially independently of said flexible sealing lip such that said flexible sealing lip may be deformed without deforming said resilient sealing pad;
    wherein said compressible material is configured to compress when said patient interface is sealed against said user's face; and
    wherein the resilient sealing pad and flexible sealing lip are configured to be attached to a patient interface by compressing within a cavity extending at least partially around an opening at an edge of a patient interface.

6. A cushion according to claim 5 wherein said resilient sealing pad comprises a foam cushion.

7. A cushion according to claim 5 wherein said flexible sealing lip is a sealing membrane substantially covering, and substantially thinner than, said resilient sealing pad.

8. A cushion according to claim 5 wherein said flexible sealing lip has a periphery that has a bead that connects in use to a substantially similar bead formed in said patient interface, in use said resilient sealing pad being disposed between said flexible sealing lip and said patient interface.

9. A cushion according to claim 5 wherein said flexible sealing lip and said resilient sealing pad each have an inner periphery, the inner periphery of said flexible sealing lip extending in use beyond that of the resilient sealing pad.

10. A cushion, configured for use with a patient interface that is configured to supply gases to a user, comprising:
    a resilient sealing pad; and
    a flexible sealing lip, adapted to engage about said resilient sealing pad,
    wherein said resilient sealing pad is adapted to deform substantially independently of said flexible sealing lip such that said flexible sealing lip may be deformed without deforming said resilient sealing pad;
    wherein said resilient sealing pad and said flexible sealing lip are independently attachable to a frame of a patient interface; and
    wherein edges of the resilient sealing pad and the flexible sealing lip are configured to extend into a cavity at least partially surrounding an opening a patient interface to secure the resilient sealing pad and flexible sealing lip to the patient interface.

11. A cushion according to claim 10 wherein said resilient sealing pad comprises a foam cushion.

12. A cushion according to claim 10 wherein said flexible sealing lip is a sealing membrane substantially covering, and substantially thinner than, said resilient sealing pad.

13. A cushion according to claim 10 wherein said flexible sealing lip has a periphery that has a bead that connects in use to a substantially similar bead formed in said patient interface, in use said resilient sealing pad being disposed between said flexible sealing lip and said patient interface.

14. A cushion according to claim 10 wherein said flexible sealing lip and said resilient sealing pad each have an inner periphery, the inner periphery of said flexible sealing lip extending in use beyond that of the resilient sealing pad.

* * * * *